(12) United States Patent
Zhang et al.

(10) Patent No.: US 11,751,997 B2
(45) Date of Patent: Sep. 12, 2023

(54) IMPLANT AND A METHOD OF MAKING THE IMPLANT AND A METHOD OF CALCULATING POROSITY OF A POROUS MATERIAL

(71) Applicants: b-ONE Medical (Suzhou) Co., Ltd., Suzhou (CN); b-ONE Medical Biotech Corporation, Shanghai (CN); b-ONE Ortho, Corp, Cedar Knolls, NJ (US)

(72) Inventors: Zongtao Zhang, Cedar Knolls, NJ (US); Imants Liepins, Cedar Knolls, NJ (US); Michael Lowry, Cedar Knolls, NJ (US)

(73) Assignees: b-ONE Medical (Suzhou) Co., Ltd., Suzhou (CN); b-ONE Medical Biotech Corporation, Shanghai (CN); b-ONE Ortho, Corp, Cedar Knolls, NJ (US)

( * ) Notice: Subject to any disclaimer, the term of this patent is extended or adjusted under 35 U.S.C. 154(b) by 816 days.

(21) Appl. No.: 16/653,921

(22) Filed: Oct. 15, 2019

(65) Prior Publication Data

US 2021/0106426 A1 Apr. 15, 2021

(51) Int. Cl.
*B33Y 50/02* (2015.01)
*B33Y 10/00* (2015.01)
(Continued)

(52) U.S. Cl.
CPC ............ *A61F 2/30942* (2013.01); *A61F 2/28* (2013.01); *A61L 27/04* (2013.01); *A61L 27/08* (2013.01);
(Continued)

(58) Field of Classification Search
CPC .................. B33Y 50/02; B22F 10/85; A61F 2002/30985; A61F 2002/30948
See application file for complete search history.

(56) References Cited

U.S. PATENT DOCUMENTS 5,282,861 A * 2/1994 Kaplan ................... B22F 3/114
623/23.51
7,875,342 B2 * 1/2011 Smith ..................... A61P 19/00
428/315.7
(Continued)

FOREIGN PATENT DOCUMENTS

CN 103537015 A 1/2014
CN 105559947 A 5/2016
(Continued)

OTHER PUBLICATIONS

Turnbull et al. 3D bioactive composite scaffold for bone tissue engineering. Bioactive Materials (2017) pp. 1-37 (Year: 2017).*
(Continued)

*Primary Examiner* — Cachet I Proctor
(74) *Attorney, Agent, or Firm* — HAMRE, SCHUMANN, MUELLER & LARSON, P.C.

(57) ABSTRACT

A method of making an implant having a porous portion is disclosed. The method comprises the following steps: obtaining an artificial foam containing porous portion; scanning the artificial foam to obtain a digital porous model; editing the digital porous model; assembling the digital porous model to form a digital porous block; editing the digital porous block to obtain a digital implant model; forming the implant by printing the digital implant model through a 3D printer. An implant and a method of calculating porosity a porosity of a porous material are also disclosed.

17 Claims, 11 Drawing Sheets

(51) Int. Cl.
*A61L 27/56* (2006.01)
*A61F 2/30* (2006.01)
*A61L 27/36* (2006.01)
*A61F 2/28* (2006.01)
*A61L 27/04* (2006.01)
*A61L 27/08* (2006.01)
*B22F 10/85* (2021.01)

(52) U.S. Cl.
CPC ........... *A61L 27/3608* (2013.01); *A61L 27/56* (2013.01); *B22F 10/85* (2021.01); *B33Y 50/02* (2014.12); *A61F 2002/30011* (2013.01); *A61F 2002/3092* (2013.01); *A61F 2002/30948* (2013.01); *A61F 2002/30985* (2013.01); *A61F 2310/00023* (2013.01); *A61L 2420/02* (2013.01)

(56) References Cited

U.S. PATENT DOCUMENTS

| | | | |
|---|---|---|---|
| 8,843,229 | B2 | 9/2014 | Vanasse et al. |
| 10,391,550 | B2 | 8/2019 | Peters et al. |
| 10,842,634 | B2* | 11/2020 | Pasini .................... A61L 27/365 |
| 2006/0088601 | A1* | 4/2006 | Overby .................. A61L 27/10 |
| | | | 424/548 |
| 2014/0010951 | A1* | 1/2014 | Vargas ................. C23C 16/045 |
| | | | 427/2.26 |
| 2014/0025181 | A1* | 1/2014 | Vanasse ................ B33Y 50/00 |
| | | | 219/76.1 |
| 2015/0173903 | A1* | 6/2015 | Li ........................ B05D 3/0254 |
| | | | 427/2.26 |
| 2018/0296343 | A1* | 10/2018 | Wei ....................... B29C 64/106 |
| 2019/0291350 | A1 | 9/2019 | Feinberg et al. |
| 2020/0330510 | A1* | 10/2020 | Chatzistavrou ....... A61L 27/427 |

FOREIGN PATENT DOCUMENTS

| | | | |
|---|---|---|---|
| CN | 108724712 A | 11/2018 | |
| WO | 2006091097 A2 | 8/2006 | |
| WO | WO-2006091097 A2 * | 8/2006 | ........... A61F 2/0077 |
| WO | 2014006519 A1 | 1/2014 | |
| WO | 2018017369 A2 | 1/2018 | |

OTHER PUBLICATIONS

International Search Report issued in PCT/CN2020/091252, dated Aug. 26, 2020.

Murr et al., "Microstructures and mechanical properties of electron beam-rapid manufactured Ti—6Al-4V biomedical prototypes compared to wrought Ti—6Al-4V", Materials Characterization, vol. 60, Issue 2, Feb. 2009, pp. 96-105.

Turnbull et al., "3D bioactive composite scaffolds for bone tissue engineering", Bioactive Materials (2017), pp. 1-37.

* cited by examiner

IMPLANT AND A METHOD OF MAKING THE IMPLANT AND A METHOD OF CALCULATING POROSITY OF A POROUS MATERIAL

FIELD OF THE INVENTION

This invention is related to a method of making an implant with reticulated titanium porous layer as well as an implant with reticulated titanium porous layer and substrate portion by three-dimensional (3D) printing process.

BACKGROUND OF THE INVENTION

Cementless fixation has been widely used for orthopedic implant for long term survival rate. Ideal integration of bone into and onto porous layer of implants provides interlocking at implant/bone interface by bone ingrowth. Reticulated tantalum foam has similar pore structure as human trabecular bone and has clinically demonstrated good fixation and bone ingrowth results. A pore size of greater than 150 µm facilitates the ingrowth of mineralized bone. A pore diameter of 200 µm corresponds to the average diameter of an osteon in human bone, while a pore diameter of 500 µm corresponds to remodeled cancellous bone. However, tantalum is very expensive, thus limited its applications.

In contrast, titanium is more cost effective and has been shown to have high biocompatibility. A reticulated titanium foam is desirable. The methods of making porous titanium have been progressed and classified into three categories. The first class was sintered beads and metal meshes onto solid metallic substrates invented in 1980s. The second method was sintering or welding pre-made metallic foam onto metallic substrate invented in 1990s. The third method was powder coating on scaffold and sintering in 2000s, and the third was additive manufacturing or three-dimensional (3D) printing invented in recent decades. Since 3D printing method has advantage of making one-step process, it becomes the frontier technology today.

The 3D printing method is divided into into three types. The first method was mathematically calculated porous structure, which usually have regular pore and strut patterns and do not simulate the cancellous bone's random structure. The second method was computer software algorithms to automatically create random porous structures, but this method does not result in the same structure as cancellous bone. The third method was the direct reverse engineering method, in which the porous metal structure was copied from a local cancellous bone by micro-CT scan, then 3D printed metal porous structure. The direct reverse engineering method has the advantage in replication of local cancellous bone structure.

However, the direct reverse engineering method has two disadvantages. One is a large variation of bone source. Human bone has high variation in porous structure. The cortical bone is very dense structure while the cancellous bone is more porous, but bone density and porosity vary in a large range. For example, age, gender, and genetics all contribute to variation in bone structure, in addition to pathologies. Elderly patients may have must less bone density than younger skeletally mature patients in their middle age. Patients with Osteoporosis have much lower bone density than those with no osteoporosis. Another disadvantage of the direct reverse engineering method is the properties of the bone structure captured by this method is location specific and bone specific. For the same person, the bone porosity depends on location within the bony structure. Humeral bones are more porous than femoral bones, and within each bone, the density may vary exponentially along the length of the diaphysis. For a same person and some location, the bone porosity is also dependent how far from bone morrow and cortical bone radially that the image is acquired. The center portion of the cancellous bone near marrow has lower density than the cancellous bone near to the cortical bone. This variation of bone source and site-specific nature of this approach makes the direct reverse engineering method difficult to utilize and apply generally to different implants and can be expensive to characterize all the myriad variables to create a representative structure for use in large scale production of implants.

In addition, bone ingrowth and fixation have been shown to relate to the pore size and interconnectivity of a structure, but no convincing evidence exists that there is a specific advantage of reproducing the exact anatomical structure over simplified structures which have similar physical characteristics that allow bone ingrowth and vascularization. The extra complexity of the exact anatomic structures adds the need for significantly more computational resources and additionally these structures are harder to pattern into larger forms and blocks because of their anisomery. Because they do not have symmetric properties, these structures must scan larger regions which are digitally acquired at lower resolution by necessity or they must scan many multitudes of sites at high resolution by dissecting and extracting from small blocks of a larger bone which is costly, time consuming, and does not solve the patterning problem in itself.

There is an additional technical challenge to quantitatively measure strut thickness, pore diameter, and porosity in real implant component. The current method to measure porous titanium is ASTM F1854-15, "Standard Test Method for Stereological Evaluation of Porous Coatings on Medical Implants". This method is a 2D method, using two-dimensional signal to estimate three-dimensional signal. The method requires physically cutting the component and manually measuring strut cross-sections area. This is labor intensive and is prone to errors. On the other hand, ASTM F3259-17, "Standard guide for Micro-computed tomography of tissue engineered scaffold." has been widely used for polymer and ceramics but is not recommended for use with porous metals because metallic artifacts significantly increase measurement errors.

It is desirable to find a good method to quantitively measure the reticulated titanium foam structure by Micro-CT method.

SUMMARY

It is an object of the present invention to provide a relatively low cost porous implant and a method of making the implant relatively inexpensive. Another object of the present invention is to provide a method capable of more accurately measuring the porosity of a porous material.

In order to achieve the above object, according to one aspect, the present invention provides a method of making an implant having a porous portion, comprising:

obtaining an artificial foam containing porous portion;

scanning the artificial foam to obtain a digital porous model;

editing the digital porous model;

assembling the digital porous model to form a digital porous block;

editing the digital porous block to obtain a digital implant model;

forming the implant by printing the digital implant model through a 3D printer.

In one embodiment, the step of editing the digital porous model comprises editing strut thickness and/or pore diameter of the digital porous model.

In another embodiment, the step of editing the strut thickness and/or pore diameter in the digital porous model comprises scaling-up or shrinking-down the strut thickness and/or the pore diameter.

In another embodiment, the step of assembling the digital porous model to form the digital porous block comprises patterning the digital porous model.

In another embodiment, the step of assembling the digital porous model to form the digital porous block comprises patterning the digital porous model along three dimension of a Cartesian coordinate, a column coordinate, or a spherical coordinate.

In another embodiment, the step of assembling the digital porous model comprises extracting an elementary porous unit from the digital porous model and combining a plurality of elementary porous units to form the digital porous block.

In another embodiment, the step of editing the digital porous block comprises cutting the digital porous block into a digital porous layer and overlaying the digital porous layer onto a substrate to form the digital implant model.

In another embodiment, the shape of the digital porous layer conforms to the shape of the implant to be formed, and the substrate conforms to the shape of the implant to be formed.

In another embodiment, the step of overlaying the digital porous layer onto the substrate is accomplished by Boolean intersection.

In another embodiment, the substrate is a solid substrate or a porous substrate.

In another embodiment, the artificial foam containing porous portion is cut into a cube geometry prior to scanning.

In another embodiment, the cube has a volume of less than 0.5 cubic inches.

In another embodiment, scanning the artificial foam to obtain a digital porous model is accomplished by micro-CT.

In another embodiment, the implant is further cleaned after 3D printing.

In another embodiment, the implant is further grit blasted and/or coated after 3D printing.

In another embodiment, the reticulated foam is selected from any of the following foams: polyurethane foam, carbon foam, ceramic coated carbon foam, metal coated carbon foam.

In another embodiment, the reticulated foam is selected from any of the following: aluminum coated carbon foam, copper coated carbon foam, nickel coated carbon foam, silicon carbide coated carbon foam, tantalum coated carbon foam, titanium nitride coated carbon foam, titanium carbide coated carbon foam, chromium coated carbon foam.

According to another aspect, the invention provides an implant, wherein the implant has a substrate and a porous portion overlapping the substrate, the implant being made through the following steps:

obtaining an artificial foam containing porous portion;

scanning the artificial foam to obtain a digital porous model;

editing the digital porous model;

assembling the digital porous model to form a digital porous block;

editing the digital porous block to obtain a digital implant model;

forming the implant by printing the digital implant model through a 3D printer.

According to yet another aspect, the invention provides a method of calculating a porosity of a porous material, the method comprising the steps of:

obtaining a first porosity by measuring a porosity of the porous material by micro-CT scan;

obtaining an actual porosity by multiplying the first porosity by a porosity calibration factor.

In one embodiment, the porosity calibration factor is obtained by the following steps:

3D printing a first sample of a porous material and obtaining a true porosity of the first sample by a gravimetric and volumetric methodology; 3D printing a second sample of the porous material and measuring the porosity of the second sample by micro-CT scan;

the true porosity of the first sample being divided by the porosity of the second sample so as to obtain the porosity calibration factor.

In one embodiment, the first sample is a cube, and the second sample is a disc.

As compared to prior art, the novelty of this invention includes the following aspects.

(1) Selection of reticulated artificial foam for micro-CT scan instead of human bone in pre-arts. This step avoided using human cadavers and is not site specific. Foam is more homogenous but more consistent and represents clinically demonstrated structures.

(2) Scale-up or shrink-down pore structure. A process is applied to adjust pore structure by scaling-up or shrinking-down the resulting 3-dimensional file. Pore diameter and strut size can be tailored to different sites of implants by using one micro-CT scan. This is contrasting to and more efficient than prior art (U.S. Pat. No. 8,843,229) that scanned multiple positions of human cadavers to fit different sites of implants.

(3) Digital assembly of foam. A small elementary porous cube will be used to pattern in X, Y and Z directions to create a larger structure from which to merge into implant structures. An overlap may be used to ensure no large asperities or gaps will be present or the geometry may be mirrored or patterned and then the larger block may be used to Boolean intersect with the 3D bodies to create the final form. One advantage of this approach is the minimization of the size of digital file and cost effectiveness in producing a structure which has been shown to meet the criteria for integration and fixation.

(4) Creation of the titanium foam structure with 3D printing technology. For example, Direct Metal Laser Sintering (DMLS) is used, which is a form of metal 3D printing technology.

(5) Micro-CT inspection. A calibration method was discovered to overcome metal artifacts of micro-CT to more precisely measure strut thickness, pore diameter, and porosity in three dimensions.

The above novelties were discovered during the execution of this invention. Three unexpected results were found. First, the direct reverse engineering approach did not work well for highly porous reticulated foam. The extremely high surface area of the foam and large volume geometry of orthopedic implants made the digital file too large to store and operate on using typical workstations and laptop computers. To solve the problem, the inventor first scan a large size of reticulated foam by high resolution micro-CT scan, then extracted a small volume as elementary volume as a building block. Using software tools, many elementary volumes were patterned into a large block which is large enough to accept the maximum implant size in the family of implant sizes. Then, Boolean geometry was used to create the final geometry from the large block by means of an Intersection function. An alternative method may be used by was directly patterning even smaller unit cells extracted from the original scan within a volume.

Another unexpected result was that the strut size, pore diameter, and porosity were not able to be replicated by direct reverse engineering. The commercially available reticulated foams were made for other engineering applications, not for orthopedics. The pore structures were limited, the specific human sites of implants were multiple, and the resolution of 3D printing process was limited by laser beam width and other DMLS parameters. These three challenges required a trial-and-error approach to obtain a preferred porous structure with the mechanical and structural parameters that match the needs of the application. This method is cumbersome and needs a lot of experiments. Instead, the inventor used a scale-up or shrink-down approach in digital editing stage for optimization of the pore structure and porosity. As a result, only three experiments obtained the optimal strut size, pore diameters, and porosity.

The third unexpected result was the calibration of micro-CT method. Engineers have struggled for decades to accurately measure porous metal structure using micro-CT method, due to metal artifacts. The metal artifacts artificially overestimate strut thickness, thus these methods typically historically resulted in lower pore diameter and porosity than the actual porosity. In this invention, a porous titanium cube's true porosity was accurately measured by using a gravimetric and volumetric methodology. The porosity ratio is defined as the true porosity divided by the measured porosity. Once determined empirically by use of a known porous structure, this calibration factor can be applied to the titanium specimens to accurately calibrate strut thickness, pore diameter, and porosity of the structure. The calibrated data were consistent with the direct experimentally measured results.

The novelty and Inventiveness of this invention will be further described in the detailed descriptions and examples.

BRIEF DESCRIPTION OF THE INVENTION

DETAILED DESCRIPTION OF THE EMBODIMENTS

The preferred embodiments of the present invention will be described in detail below with reference to the accompanying drawings, so that the purposes, features and advantages of the present invention can be more clearly understood. It should be understood that the embodiments shown in the accompanying drawings are not intended to limit the scope of the present invention, and is only used for illustrating the essential spirit of the technical solution of the present invention.

In the following description, numerous specific details are set forth. However, one skilled in the art may implement embodiments without these specific details. In other instances, well-known devices, structures, and techniques that are associated with the present application may not be shown or described in detail to avoid obscuring the embodiments.

Unless the context indicates otherwise, the words "comprise" and variations thereof, such as "include" and "have", are meant to be construed as an open, inclusive meaning, that is, not limited to.

Figure 1:
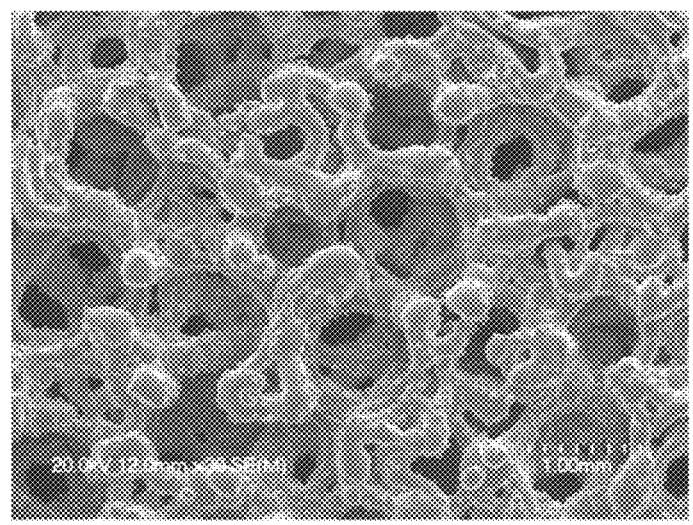
FIG. 1 is a diagram illustrating a reticulated titanium porous structure.
Figure 2:
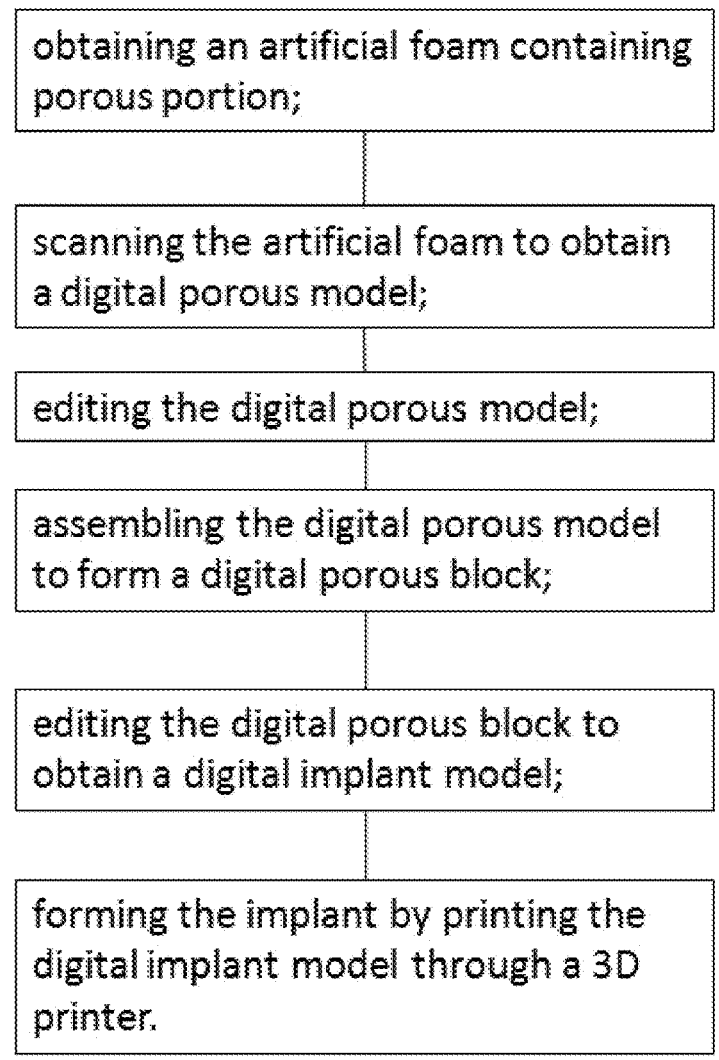
FIG. 2 is a flow chart illustrating a process of making an implant.

FIG. 2 is a flow chart illustrating a process of making an implant. The first step of this invention is the selection of source of porous structure. In general, all reticulated artificial foams have connected porous and open pore structure can be selected for micro-CT scan, such as polyurethane foam, carbon foam, aluminum coated carbon foam, copper coated carbon foam, nickel coated carbon foam, silicon carbide coated carbon foam, tantalum coated carbon foam, titanium nitride coated carbon foam, titanium carbide coated carbon foam chromium coated carbon foam etc. All these foams are commercially available. Tantalum coated carbon foam has been approved for bone growth, but the atomic weight is so high that micro-CT will generate a lot of artifacts. Low atomic foams such as polyurethane foam has low atomic weight, but flexible so the porous structure easily distorted during holding for Micro-CT scan. The preferred reticulated porous foam are ceramics or metal coated carbon foams with low atomic numbers. The preferred ceramics are such as reticulated Al2O3, mullite, SiC, MgO, CaO, hydroxyapatite, Zirconia etc. The preferred metal foams are aluminum coated carbon foams, copper coated carbon foam, nickel coated carbon foam, silicon carbide coated carbon foam. The most preferred is reticulated SiC coated carbon foam.

Reticulated carbon and SiC coated carbon foams have different porosities. They are measure by pores per inch (PPI). The commercial SiC foams have porosity range of 3 PPI, 10 PPI, 20 PPI, 30 PPI, 45 PPI, 65 PPI, 80 PPI, and 100 PPI (Ultramet INC, 1217 Montague Street, Pacolma, Calif.

91331, USA). The lower the number PPI, the larger the diameters of pores and pores. The carbon foam are fragile, so silicon carbide coated carbon forms (briefly called SiC foam) are stronger, especially in high PPI number of foams. In theory, all porous foams are theoretically selected as sample of scan. 65 PPI, 80 PPI, and 100 PPI foams are preferred because they are close to the porosity of cancellous bone.

Figure 3:
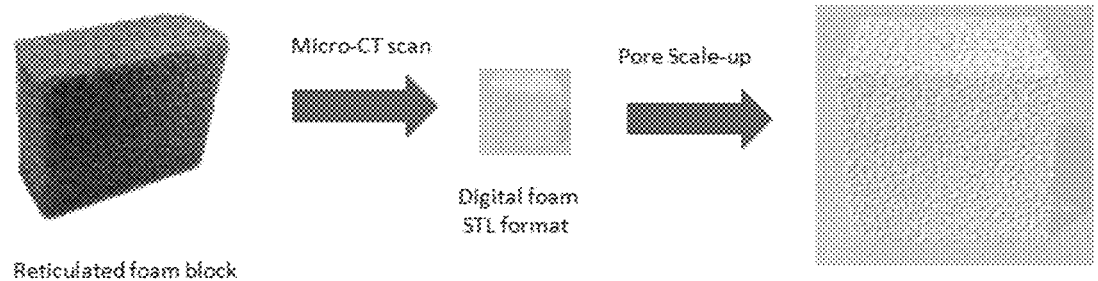
FIG. 3 is a diagram illustrating Micro-CT scanning of a reticulated artificial foam and pore scaling-up in digital file

See FIG. 3, the second step is micro-CT scanning of reticulated foam and save the scan into a digital foam, that is, save the scan as a digital porous model. Any Micro-CT scanner with high resolution can be used for scanning. The finer the micro-CT scanning, the more detailed strut structure can be observed. However, the scanning time will be longer, the STL file will be larger. Considering the powder size of additive manufacturing are 25 to 100 microns in average diameter, the preferred micro-CT scan voxel are selected in 20 micrometers to 40 micrometers range. The most preferred micro-CT scan voxel is 20 micrometers.

Figure 4:
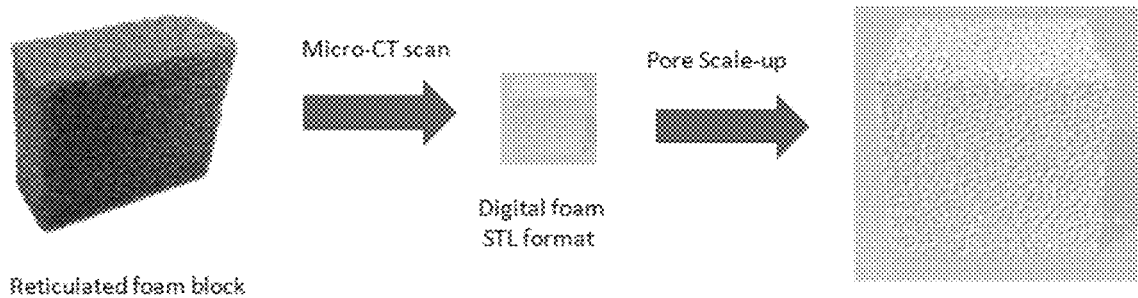
FIG. 4 is a diagram illustrating digital assembling a digital cube into a porous layer.
Figure 5:
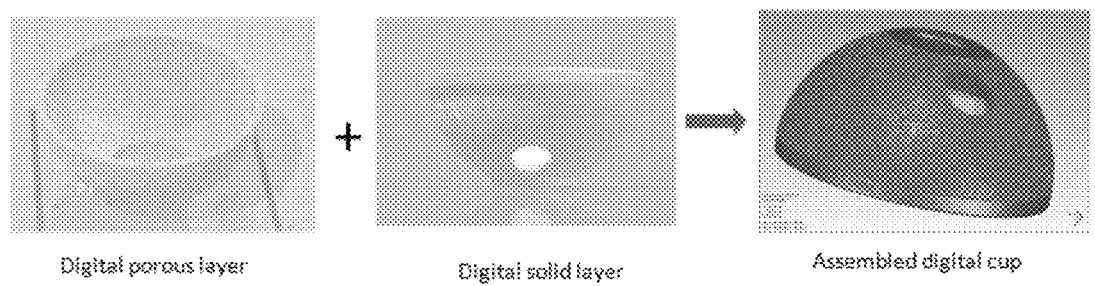
FIG. 5 is a diagram illustrating porous layer being assembled with solid substrate into a digital acetabular shell.

The most popular way was direct reverse engineering approach, which directly replicates the porous structure. Table 1 shows the micro-CT scan results of three 80 PPI carbon, 80 PPI SiC, and 65 PPI SiC. FIG. 3-5 show the strut thickness and pore distributions of 80 PPI SiC foam. All these three foams have very high open porosity and capable for micro-CT scan to achieve digital files. The average carbon strut was 56.4 micron, too fragile to hand. Because SiC was coated on the carbon foam, the strut thickness increased to about 100 µm, so SiC foam is preferred. The 80 PPI SiC has 78.7% porosity and all pores are open. The strut thickness 98.2±27.2 µm and pores diameter 303±98 µm. Pores over 150 µm is more than 93% in volume, which facilitate the ingrowth of mineralized bone. However, these strut diameter, pore diameter and porosity are limited to the original source of choice.

TABLE 1

STL size, strut thickness, pore diameter, porosity, and open porosity of ½" reticulated artificial cube by Micro-CT scan.

| Reticulated foams | 80 PPI Carbon | 80 PPI SiC | 80 PPI SiC | 65 PPI SiC |
|---|---|---|---|---|
| Voxel of micro-CT | 20 µm | 20 µm | 40 µm | 40 µm |
| STL file size | N/A | 440,831 KB | 195,500 KB | 180,602 kB |
| Strut thickness | 56.4 ± 17 µm | 9 ± 8.2 ± 27.2 µm | 126 ± 40 µm | 149 ± 31 µm |
| Pore diameter | 483 ± 120 µm | 303 ± 98 µm | 398 ± 94 µm | 712 ± 153 µm |
| Open porosity | 93.9% | 78.7% | 76.76% | 82.76% |
| Total porosity | 93.9% | 78.7% | 76.76% | 82.76% |

The inventor also tried direct reverse engineering approach for final geometry. the inventor customized 80 mm×80 mm×80 mm reticulated Carbon or SiC coated carbon cube, machined the cube into the 68 mm OD and 1.5 mm shell, then micro-CT scanned the shell. The cost is very high.

To solve the cost issue, the inventors tried a micro-CT scan 1.0" SiC foam with cube geometry (25.4 mm×25.4 mm×25.4 mm). After micro-CT scanning using 20 µm Voxel resolution, the scan engineer tried to extract the scan data to STL file format, but the STL file size was too big to handle by even a supper computer. Finally, the inventor tried to take out 0.5" cube (12.5 mm×12.5 mm×12.5 mm) data from the 1.0" cube, the file size was smaller, then a lap-top computer was successfully saved the STL file.

The third step of the method is editing the digital porous model, see FIG. 3. For example, the dimension and the shape of the digital porous model may be edited. Particularly, the strut and pore size of the STL file of the porous foam was edited. For example, the strut and pore size of the STL file of the porous foam was scaled-up or shrink-down. The final printed foam porosity and strut size may be different from any of original scanned foam. This process was scanning one reticulated foam only, obtaining STL file, then digitally scale-up or shrink-down the STL file. Based on digital imaging and final 3D printing, to find the optimum pore and strut structure. This approach can adjust pore structure with unlimited range and fit any position bone in the human body.

Table 2 lists a theoretical range of pore sizes based on different scaling up or shrink-down scale. This value is the guideline for initial selection of SiC or Carbon foam, not final size of 3D printed foam. In theory, any reticulated artificial foam can be selected as micro-CT scan sample to get digital porous structure, through shrink-down (scale factor <1.0) from larger pore foams such as 3 PPI, 10 PPI, 20 PPI, 30 PPI, 40 PPI, or scale-up (scale factor >1.0) such as 80 PPI, 100 PPI. The preferred pore size is close to as desired pore size and make adjustment through scaling, such as 65 PPI, 80 PPI, and 100 PPI foams were selected for micro-CT scan.

TABLE 2

Theoretical pore diameter with different scale-up scales.

| Scale factor | 0.1 | 0.4 | 0.6 | 1.00 | 1.25 | 1.50 |
|---|---|---|---|---|---|---|
| 3 PPI foam | 846 µm | | | | | |
| 20 PPI foam | 127 µm | 508 µm | 762 µm | | | |
| 45 PPI foam | | 225 µm | 338 µm | 564 µm | 705 µm | 846 µm |
| 65 PPI foam | | 156 µm | 234 µm | 391 µm | 489 µm | 587 µm |
| 80 PPI foam | | | 190 µm | 317 µm | 397 µm | 476 µm |
| 100 PPI foam | | | 152 µm | 254 µm | 317 µm | 381 µm |

The fourth step of the method is digital assembly small porous foam into final implant geometry, forming a digital implant model, see FIGS. 4-5. For example, a STL file of 0.5" cube after pore structure scale-up or shrink-down was selected as a building block. Many 0.5" cube STL blocks were digitally overlapped each other to form a larger block by a 3D editing software. This larger block is a digital porous block. The digital porous block was cut into a digital shell with multi holes. The digital porous layer was laid on a solid substrate or a porous substrate with overlap to form a final acetabular shell for cement-less fixation, see FIG. 5. In theory, any shape of porous foam can be cut out from the digital porous block. Alternatively, a very small digital block can be cut out from the ½" cube from any coordinate, such as spherical coordinate or column coordinate. The small block can be digitally assembled to any shape of components. The commercial software are available for the digital assembly. The examples are Geomagic Wrap®, Materilise Magics®, 3D Expert®, etc.

The large digital blocks can be cut to any desired geometry for implants or bone fillers. The inventor found that the overlap of the STL building block is necessary. If just line-to-line assembly, the 3D printed samples will have visible line or gap. The digital reconstruction includes porous layer to solid layer as well. A minimum 1.0 µm overlap is needed, preferred over 10 μm overlap, more preferred over 50 μm, the most preferred over 100 μm overlap.

Based on theoretical teaching of 3D printing and pre-arts, the overlap of STL file were not desirable. It would generate a lot of suspended overhanging struts and non-closed loops. The computer software would consider the overlap as errors and need to repair. Surprisingly, the inventers has not found any visual mark, no effect on mechanical properties and porosity.

The fifth step of the method was 3D printing. Sending the assembled acetabular cup model to a 3D printer. The 3D printing is the state-of-the art technology by lay-by-layer melting or sintering process under laser or e-beam as heating source. The 3D metal printers were commercially available, such as M2 Cursing DL 400 W, ProX DMP320, FARSON 271 M, BLT-5310. Any one of them can be used for 3D printing the reticulated titanium porous implant. During this process, a software convert STL file into slicing file, then printed into final geometry. After 3D printing, the final acetabular shell was removed metal supports, grit blasting, mechanical vibration and ultrasonic cleaning to remove loss powder inside of the porous layer. A post grit blasting and coating process such as coating hydroxyapatite can be conducted on the porous surface.

Figure 7:
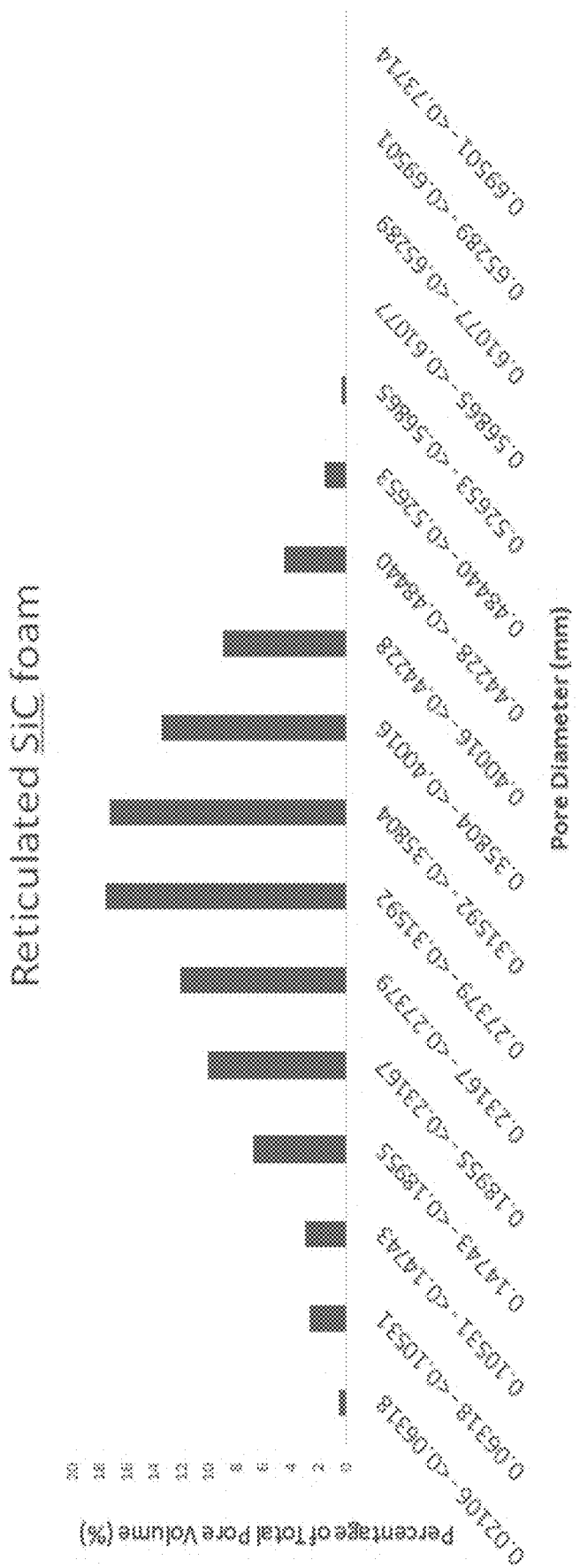
FIG. 7 is a diagram illustrating volume percentage of three-dimensional pore diameters of 80 PPI reticulated SiC foam by micro-CT with 20 Voxel resolution.

The six-step was micro-CT inspection of porous structure. ASTM F3259-17, "Standard guide for Micro-computed tomography of tissue engineered scaffold" has been widely used for polymer and ceramics with high accuracy to measure strut size, pore size, and porosity. FIG. 7 shows the three-dimensional pore diameters of 80 PPI reticulated SiC foam by micro-CT scan. The measured average 316 μm pore size is consistent to the theoretical calculation 317 μm in Table 1. However, this method has not recommended to metal because the metallic artifacts. The metallic artifacts caused a thicker struts (about 25 μm), smaller pore diameters (about 140 μm), and lower porosity (about 15%) than their real value (Table 3). The metal artifacts traditionally minimized by increasing X-ray energy, but still generated a large error, thus not recommended by ASTM for measure porous titanium porous layer yet.

TABLE 3

Reticulated Ti6Al4V porous structure measured by micro-CT and light microscopy before artifacts calibration.

|  | Example 1 | Example 2 | Example 3 |
|---|---|---|---|
| Strut thickness (micro-CT), μm | 260 ± 53 | 258 ± 56 | 236 ± 58 |
| Strut thickness (Light microscopy), μm | 239 ± 38 | 226 ± 40 | 213 ± 58 |
| Pore Diameter (Micro-CT, 3D), μm | 242 ± 84 | 325 ± 118 | 396 ± 155 |
| Pore Diameter (Light microscopy, 2D), μm | 350 ± 60 | 458 ± 68 | 562 ± 82 |
| Total Porosity (Micro-CT), % | 35.5 | 46.82 | 56.13 |
| Total Porosity (weight and volume), % | 50.38 |  |  |
| Open porosity/Total porosity (Micro-CT), % | 100 | 100 | 100 |

Instead avoiding the artifacts like pre-arts, the inventor used the artifacts as a calibration tool. The inventor define a calibration factor for micro-CT as below:

Porosity calibration factor=porosity of first sample (weight and volume)/porosity of second sample (micro-CT)

Pore diameter calibration factor=Porosity calibration factor

Strut thickness calibration factor=$(1/\text{Pore diameter calibration factor})^{1/3}$ Here, a ½" cube is used as first sample and as calibration. The true porosity of the ½" porous cube was 50.38%, which was accurately measured weight and volume method. The details were described in Example 7. The porosity calibration factor is 1.419, equal to the ratio of cube porosity 50.38% divided second sample porosity 35.5%. In this example, the second sample is a disc) Pore diameter calibration factor is equal to Porosity calibration factor, 1.419. Strut thickness calibration factor is equal to $(1/1.419)^{1/3} = 0.8896$. The calibrated results were listed in Table 4, which were consistent with the light microscopy measurement data.

It should be understood that other shapes than cubes and discs, such as cuboids, ellipses, etc., may be employed to calculate the porosity calibration factor. As long as the first sample is 3D printed and a true porosity of the first sample is obtained by a gravimetric and volumetric methodology, and the second sample is 3D printed and a porosity of the second sample is measured by micro-CT scan, then the true porosity of the first sample being divided by the porosity of the second sample so as to obtain the porosity calibration factor.

TABLE 4

Reticulated Ti6Al4V porous structure measured by micro-CT and light microscopy after artifacts calibration.

|  | Example 1 | Example 2 | Example 3 |
|---|---|---|---|
| Calibrated Strut thickness (micro-CT), μm | 231 ± 47 | 229 ± 50 | 210 ± 52 |
| Strut thickness (Light microscopy), μm | 239 ± 38 | 226 ± 40 | 213 ± 58 |
| Calibrated Pore Diameter (Micro-CT, 3D), μm | 343 ± 119 | 461 ± 167 | 561 ± 220 |
| Pore Diameter (Light microscopy, 2D), μm | 350 ± 60 | 458 ± 68 | 562 ± 82 |
| Total Porosity (Micro-CT), % | 35.5 | 46.82 | 56.13 |
| Calibrated Total porosity (Micro-CT), % | 50.38 | 66.44 | 79.65 |
| Open porosity/Total porosity (Micro-CT), % | 100 | 100 | 100 |

EXAMPLES

Example 1. Reticulated Porous Titanium Sample with 1:1 Scale Ratio to SiC Foam

A reticulated titanium porous foam with 1:1 ratio to 80 PPI SiC foam was made according to process in FIG. 2. The 80 PPI SiC foam was made by Ultramet INC (1217 Montague Street, Pacolma, Calif. 91331, USA). The SiC foam has porosity 80 pores per inch (PPI). A foam block with dimension of 30 mm×20 mm×12.5 mm was scanned by micro-CT at a voxel of 20 microns at Microphonics INC (1550 Pond Road, Suite 110, Allentown, Pa. 18104, USA). The micro-CT scan parameters of SiC foam were Bruker SkyScan 1173 micro-CT, voxel 20 μm, source voltage 100 kV, source current 62 μA. Reconstructions were completed using Bruker NRecon software, porosity analysis was done using Bruker CTAn software and STL models were made using Synopsis Simpleware software. There was no ring artifect correction, smoothing. Beam hardening correction 40%.

A ½" cube (12.5 mm×12.5 mm×12.5 mm) was digitally cut out from the original 30 mm×20 mm×12.5 mm block. The micro-CT scan was saved as STL format. Using Materalise Magics' 3D printing software, four ½" porous cubes were digitally assembled into a 1.0" porous cube (25.4 mm×25.4 mm×25.4 mm). The contact of the cubes was face-to-face contact, i.e., no overlap. Cut the 1.0" digital cubes into a disc shape with 25.4 mm diameter and 1.5 mm thickness. The porous disc was digitally assembled with a solid sample with a thickness of 25.4 mm and 6.25 mm thickness. The porous layer was overlapped 100 μm so as to form a digital model.

The digital model was printed using Ti6Al4V ELI powder by M2 Coursing 3D printing machine at GE Additive INC (101 North Campus Drive, Findlay Township, Pa. 15126, USA). During printing, the laser beam was set up 150 μm diameter. Loose powders were removed from the printed samples powders by mechanical vibration in air, followed ultrasonic cleaning in water.

The light microscopy showed gaps at the assembly lines. The struts thickness and pore diameter were analyzed by a digital light microscopy and Micro-CT. The micro-CT scan parameters of Ti6Al4V porous layer (1.5 mm thickness, 25.4 mm diameter) on 1.0" diameter solid were Bruker SkyScan 1173 micro-CT, voxel 20 μm, source voltage 130 kV, source current 60 μA.

Reconstructions were completed using Bruker NRecon software, porosity analysis was done using Bruker CTAn software and STL models were made using Synopsis Simpleware software. For minimizing metal artifacts, ring artifacts correction was grade 4, smoothing grade 2, beam hardening correction 100%.

Example 2. Reticulated Porous Titanium Sample with 1.25:1 Scale Ratio to SiC Foam All process parameters were the same as Example 1, except the digital STL file of 80 PPI SiC foam was magnified to 1.25 scale in three-dimensional geometry.

Example 3. Reticulated Porous Titanium Sample with 1.50:1 Scale Ratio to SiC Foam All process parameters were the same as Example 1, except the digital STL file of 80 PPI SiC foam was magnified to 1.5 scale in three-dimensional geometry.

Example 4. Reticulated Porous Titanium Cube with 1:1 Scale Ratio to SiC Foam

All process parameters were the same as Example 1, except the ½" digital cube was directly printed out into a Ti6Al4V porous cube.

Example 5. Reticulated Porous Titanium Shell with 1:1 Scale Ratio to SiC Foam

All process parameters were the same as Example 1, except digitally assembly a ½" porous cube (12.5 mm×12.5 mm×12.5 mm) into a porous acetabular shell with dimension of 40 mm in dimeter, 1.5 mm in thickness (FIG. 4). The porous acetabular shell was integrated the porous shell with a solid substrate into a digital acetabular cup (FIG. 5). The digital acetabular cup model was sent M2 Cursing 3D printer (GE additive) to print a physical Ti6Al4V cup. Different from samples (Example 1-3), the face-to-face contact among the cubes were eliminated. Instead, all cubes were digitally assembled with 100 μm overlap, the same overlap to solid substrate. After 3D printing, there were no visual assembly line in the porous layer.

Example 6. Reticulated Porous Titanium Steroid with 1:1 Scale Ratio to Carbon Foam All process parameters were the same as Example 1, except an steroid shaped reticulated carbon foam was micro-CT scanned for 3D printing a reticulated porous titanium steroid with 1:1 scale ratio. The porous structure of reticulated carbon foam was shown in Table 1. Due to the extremely fine strut thickness 56.4±17 μm, the 3D printer software was hard to recognize the struts. After carful adjust 3D printer parameters, a reticulated porous titanium steroid was printed out, but there were a lot of powders left inside the porous space. The printing was not successful.

Example 7. Characterization of SiC Foams and 3D Printed Components

Reticulated porous SiC foam were characterized by micro-CT scanning.

Figure 6:
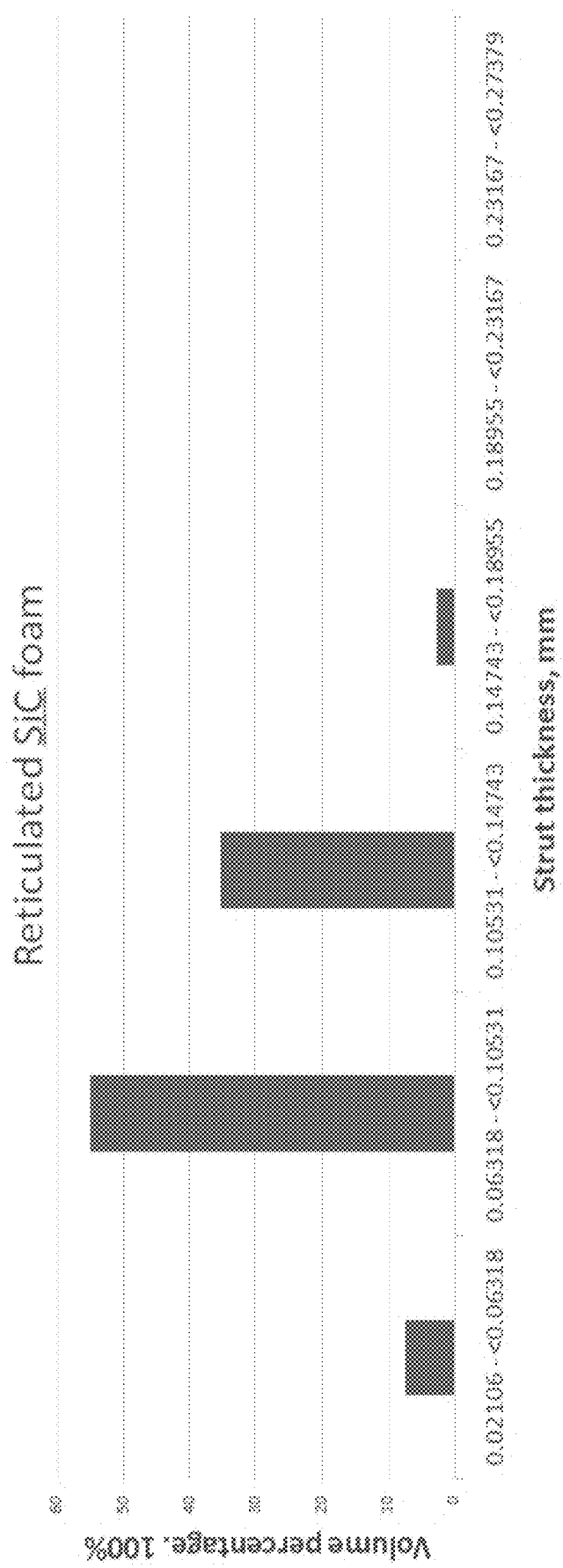
FIG. 6 is a diagram illustrating volume percentage of three-dimensional pore diameters of 80 PPI reticulated SiC foam by micro-CT method.
Figure 8:
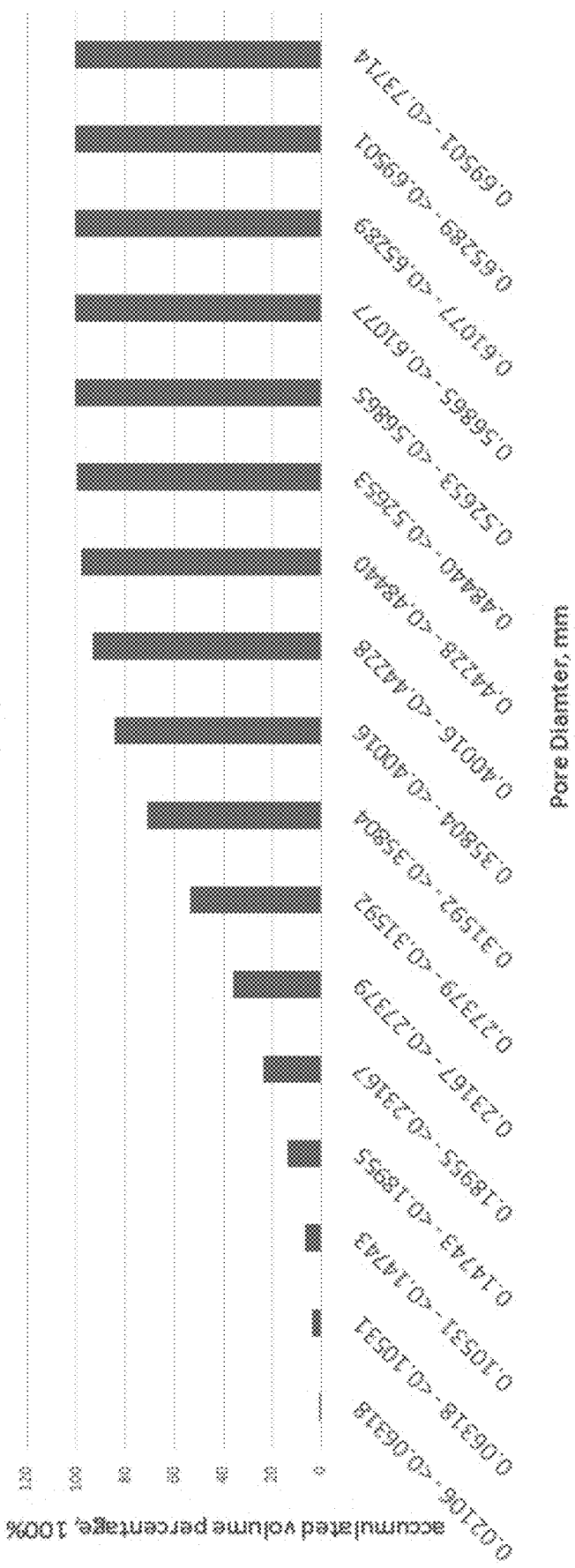
FIG. 8 is a diagram illustrating accumulated volume percentage of three dimensional pore diameters of 80 PPI reticulated SiC foam by micro-CT with 20 Voxel resolution.

Micro-CT was conducted at Microphonics INC (1550 Pond Road, Suite 110, Allentown, Pa. 18104, USA) according to ASTM F3259-17. The Micro-CT machine was Skyscan1173. The analysis used adaptive mode (mean of min and max values) with lower grey thresholding 20 and upper grey thresholding 150. FIG. 6-8 showed the characteristics of 80 PPI SiC foam structure, including strut thickness distribution, pore size distribution, and accumulated pore size distribution. Table 1 summarized results. Average pore size was 300-400 μm and open porosity of 76-78%. Because SiC coated carbon foam is ceramic with low atomic numbers, the metal artifact is negligible. The pore diameter 300-400 μm is consistent to the calculated pore diameter of 317 μm for 80 PPI number in Table 2.

The Reticulated porous titanium porous layer on samples (Example 1-3) and ½" cube (Example 4) were characterized by micro-CT scanning. Micro-CT was conducted at Microphonics INC (1550 Pond Road, Suite 110, Allentown, Pa. 18104, USA) according to ASTM F3259-17. The Micro-CT machine was Skyscan1173.

The analysis used adaptive mode (mean of min and max values) with lower grey thresholding 60 and upper grey thresholding 155. Because of titanium has metal artifacts for Micro-CT, light microscopy method was used to measure strut thickness and pore size. The weight and volume method were used to direct measure porosity of the ½" porous Ti6Al4V cube. The weighted was measured by a calibrated analytical balance with accuracy 0.1 mg. The volume was measured by a calibrated micrometer with accuracy 0.01 mm. Table 3, and Table 4 list reticulated Ti6Al4V porous structure measured by micro-CT and light microscopy before and after artifacts calibration.

Figure 9:
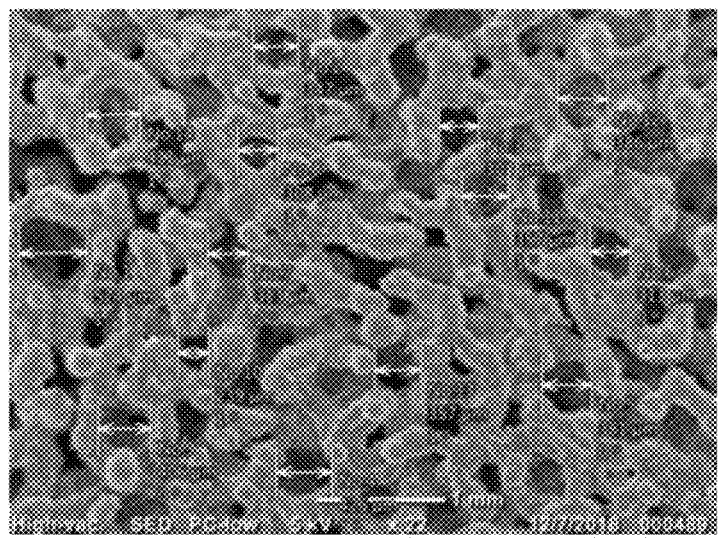
FIG. 9 is a diagram illustrating light microscopy of 3D printed reticulated Ti6Al4V foam by with Ti:SiC:=1:1 scale.
Figure 10:
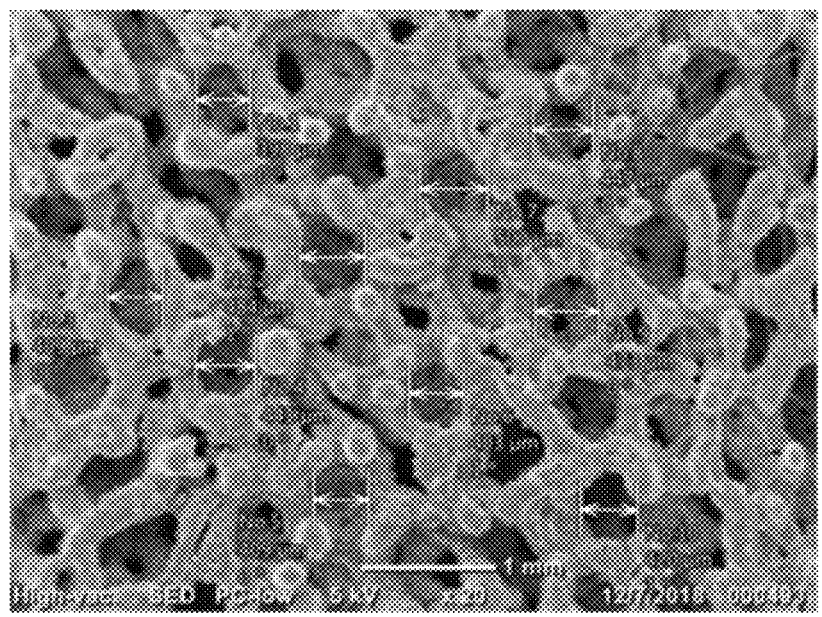
FIG. 10 is a diagram illustrating light microscope pictures of 3D printed reticulated Ti foam by light microscopy with Ti:SiC=1.25:1 scale.
Figure 11:
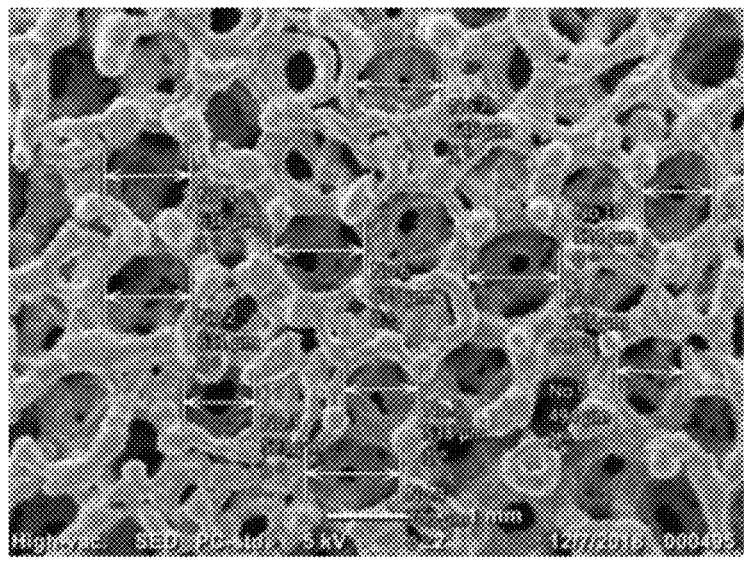
FIG. 11 is a diagram illustrating light microscope pictures of 3D printed reticulated Ti foam by light microscopy with Ti:SiC=1.5:1 scale.

FIG. 9-11 show the strut thickness of 3D printed reticulated porous titanium layers on solid titanium samples by light microscopy pictures of (Example 1-3). The struts thickness is about 220 μm with standard deviation about 50 μm, even though the titanium porous structures were scaled up to 1.25 and 1.5 scales relative to 80 PPI SiC foam. This means that the strut thickness was dominated by the laser beam diameter. The initial digital SiC foam struts thickness was 98 μm at 1:1 ratio (Table 1), the digital SiC struts were 122 µm and 147 µm after scale-up to 1.25 and 1.5 times, which were less than the minimum laser beam size setting 150 µm. The Micro-CT measured struts were thicker than the light microscope measured value about 20-30 µm due to metal artifacts (Table 1), but the artifacts were corrected based on the teaching of this invention.

FIG. 9-11 show the pore diameters of 3D printed reticulated porous titanium layers on solid titanium samples by light microscopy pictures of (Example 1-3). In contrast to strut thickness, the pore diameters increased with Ti:SiC scale ratio. The light microscopy measured pore diameters are 350±60 458±68 µm, and 562±82 µm (Table 3), which are corresponding to designed Ti:SiC scale ratio of 1, 1.25 and 1.5. The designed scale ratios are consistent to the experimental ratio of 1.0 (350/350), 1.30 (458/350), and 1.60 (560/350).

Figure 12:
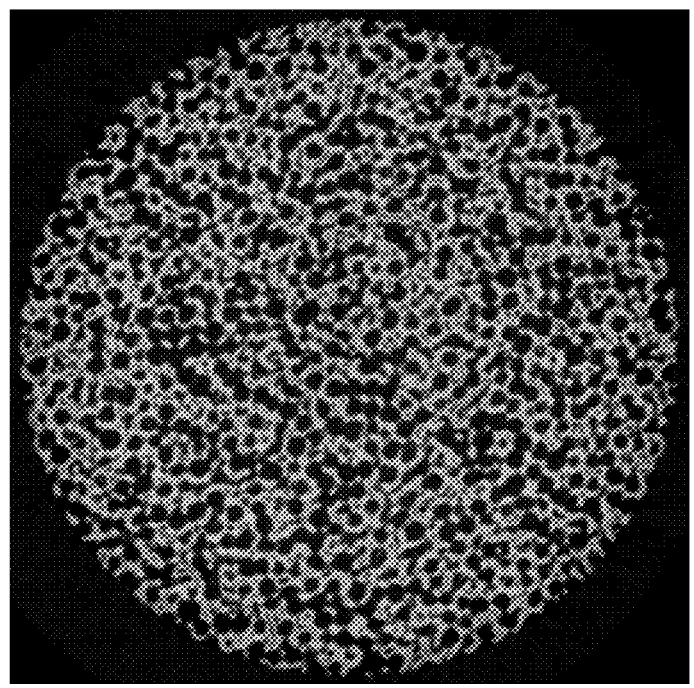
FIG. 12 is a diagram illustrating Micro-CT scan of 3D printed reticulated Ti foam, Ti:SiC=1.5:1.0 scale.
Figure 13:
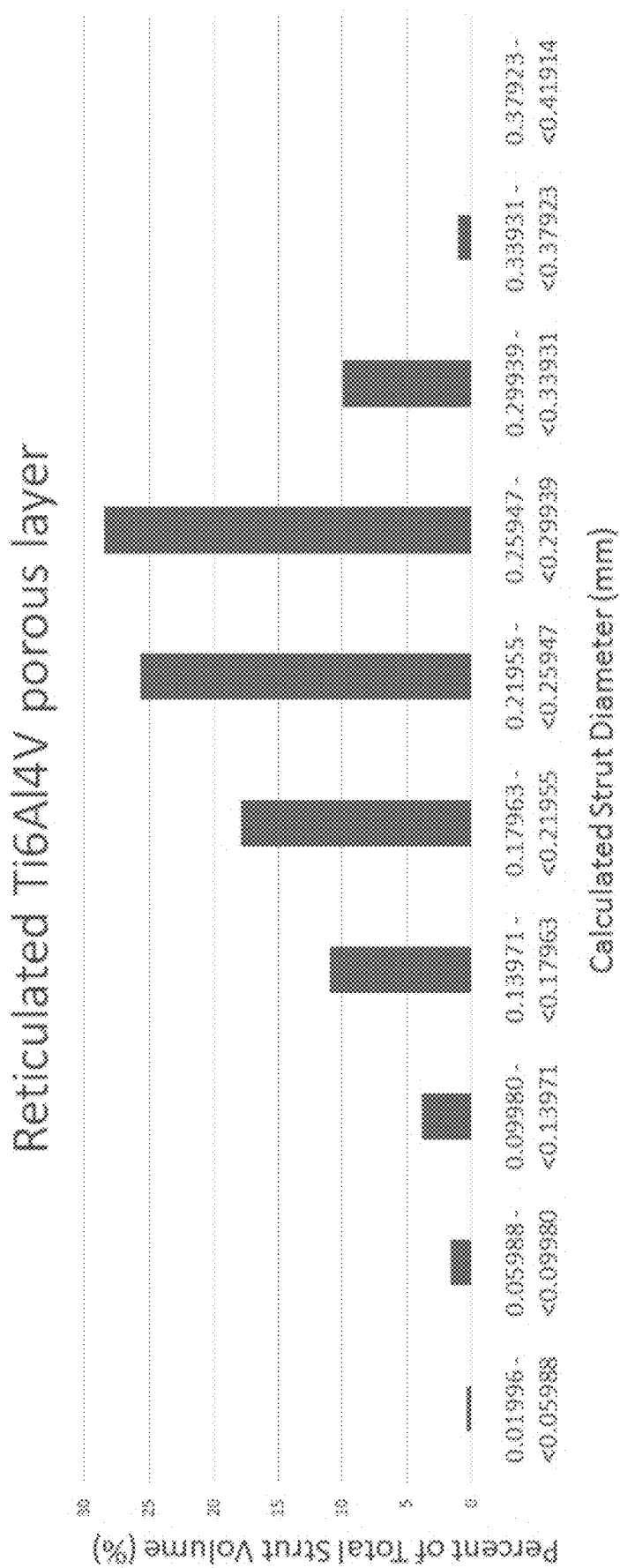
FIG. 13 is a diagram illustrating strut thickness distribution of reticulated Ti6Al4V porous layer with Ti:SiC=1.5:1 scale.
Figure 14:
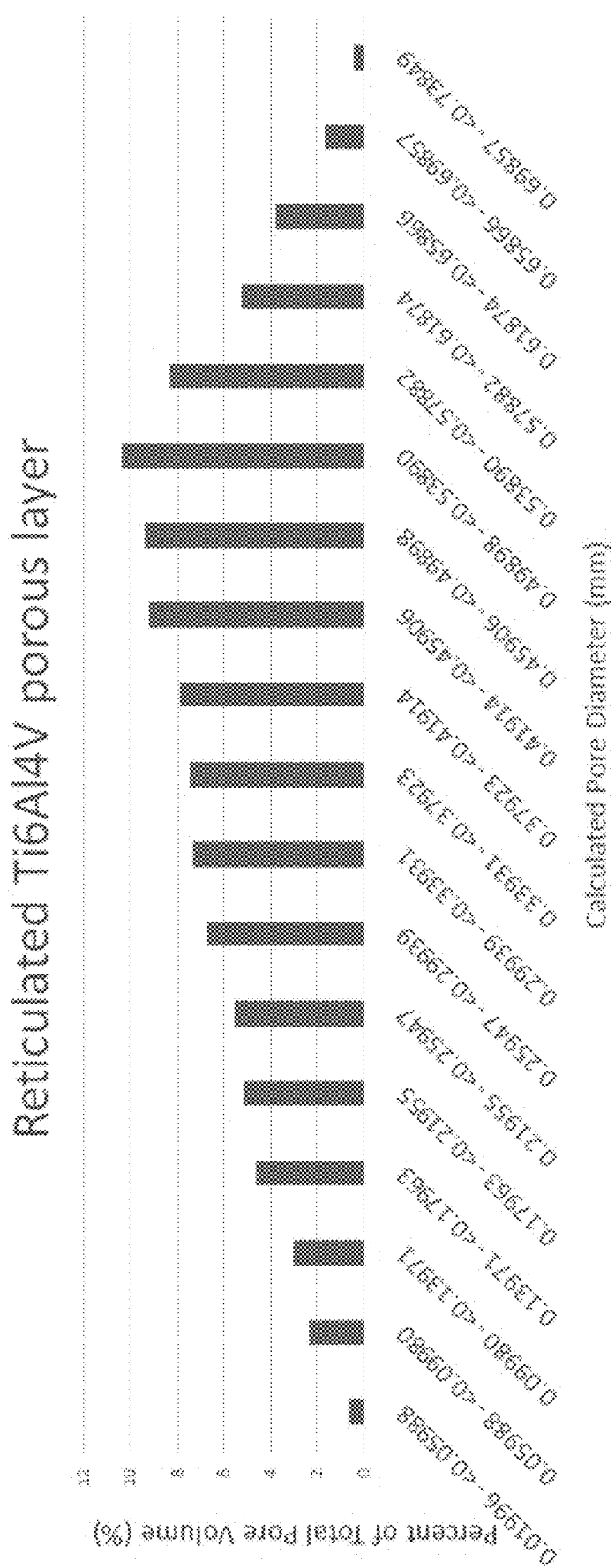
FIG. 14 is a diagram illustrating pore diameter distribution of reticulated Ti6Al4V porous layer with Ti:SiC=1.5:1 scale.
Figure 15:
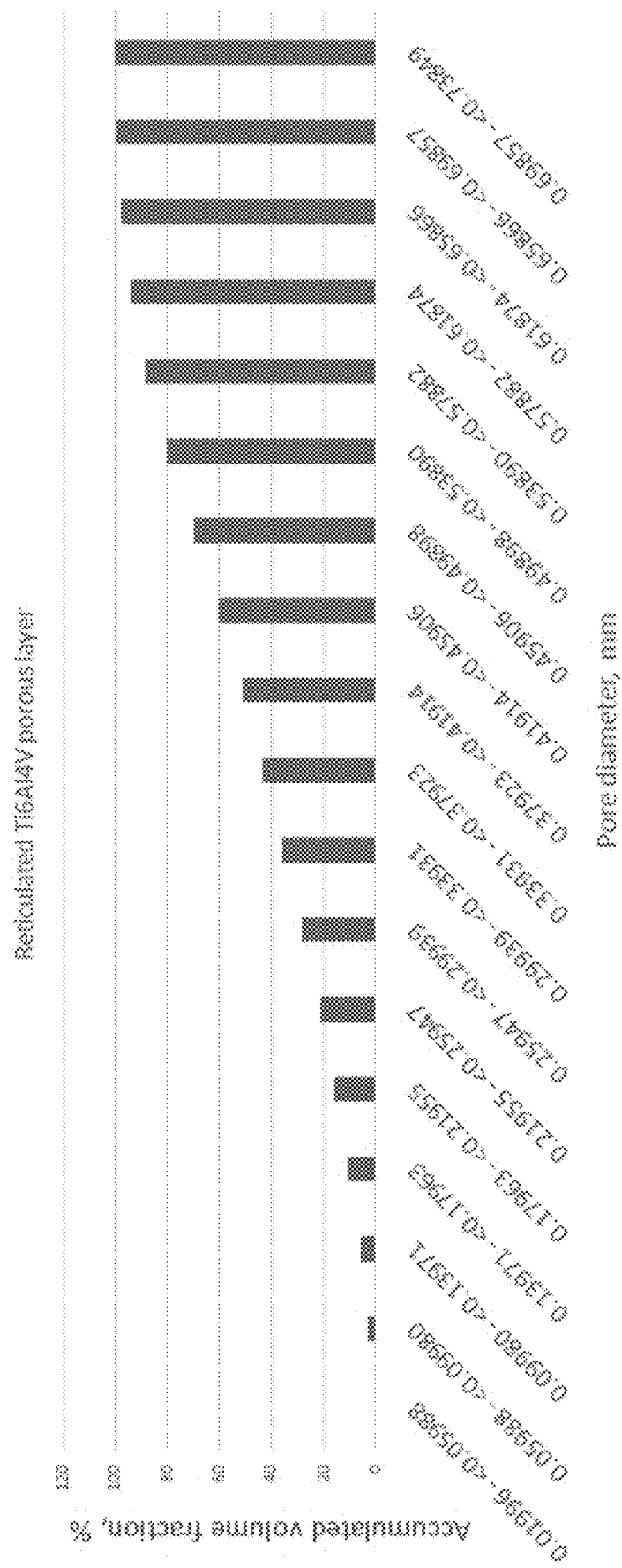
FIG. 15 is a diagram illustrating pore diameter distribution of reticulated Ti6Al4V porous layer with Ti:SiC=1.5:1 scale.

FIG. 12 shows the micro-CT scan of 3D printed reticulated Ti foam with Ti:SiC=1.5:1.0 scale. The pores were interconnected. FIG. 13-15 showed original micro-CT scan data of strut and pore diameter distributions without metal artifacts calibration. The all pores are larger than 180 µm and less than 800 Based on U.S. Pat. No. 5,282,861, the bone is preferred to growth in about 600 µm titanium pores in 400 µm, 600 µm and 800 µm range. Therefore, the preferred pore size in this invention was the sample Example 3, which has Ti:SiC scale ratio 1.5.

Table 4 listed the porosity of reticulated titanium porous layer. After artifacts calibration, the porosities are corrected to 50.38%, 66.44% and 79.65% for Example 1-3. Based on previous discussion, the scale-up process was primarily for magnification of pore diameter. The theoretical porosity value of Example 1-3 was 50.38%, 62.98%, and 75.57%, which very consistent to the calibrated porosities. These porosity value indicated that Ti:SiC 1:1 ratio is acceptable, preferred 1.25:1 ratio, the most preferred 1.5:1 ratio.

Table 5 shows the bond strength results of reticulated Ti6Al4V ELI samples. Tensile and shear bond strength were all above the FDA required minimum requirement, 20 MPa for tensile and 22 MPa for shear. All failure occurred at porous titanium/adhesive interface.

TABLE 5

Bond strength results of reticulated Ti6Al4V ELI samples

| Reticulated Ti samples | Example 1 | Example 2 | Example 3 |
| --- | --- | --- | --- |
| Shear Bond strength, MPa | 47.9 ± 3.1 | 49.3 ± 0.7 | 42.3 ± 0.8 |
| Failure mode | 100% adhesive | 100% adhesive | 100% adhesive |
| Tensile Bond strength, MPa | 76.4 ± 4.0 | 73.4 ± 6.4 | 70.6 ± 2.5 |
| Failure mode | 100% adhesive | 100% adhesive | 100% adhesive |

Preferable embodiments of the invention have been described in detail as above. It should be understood that, after reading the above teaching of the invention, various changes or modifications of the invention can be made by those skilled in the art. All of the equivalents fall in the protection scope defined by the attached claims.

What is claimed is:

1. A method of making an implant having a porous portion, comprising:
    obtaining an artificial foam containing porous portion;
    scanning the artificial foam to obtain a digital porous model;
    editing the digital porous model;
    assembling the digital porous model to form a digital porous block;
    editing the digital porous block to obtain a digital implant model; and
    forming the implant by printing the digital implant model through a 3D printer.

2. The method according to claim 1, wherein the step of editing the digital porous model comprises editing strut thickness and/or pore diameter of the digital porous model.

3. The method according to claim 2, wherein the step of editing the strut thickness and/or pore diameter in the digital porous model comprises scaling-up or shrinking-down the strut thickness and/or the pore diameter.

4. The method according to claim 1, wherein the step of assembling the digital porous model to form the digital porous block comprises patterning the digital porous model.

5. The method according to claim 1, wherein the step of assembling the digital porous model to form the digital porous block comprises patterning the digital porous model along three dimension of a Cartesian coordinate, a column coordinate, or a spherical coordinate.

6. The method according to claim 1, wherein the step of assembling the digital porous model comprises extracting an elementary porous unit from the digital porous model and combining a plurality of elementary porous units to form the digital porous block.

7. The method according to claim 1, wherein the step of editing the digital porous block comprises cutting the digital porous block into a digital porous layer and overlaying the digital porous layer onto a substrate to form the digital implant model.

8. The method according to claim 7, wherein the shape of the digital porous layer conforms to the shape of the implant to be formed, and the substrate conforms to the shape of the implant to be formed.

9. The method according to claim 7, wherein the step of overlaying the digital porous layer onto the substrate is accomplished by Boolean intersection.

10. The method according to claim 7, wherein the substrate is a solid substrate or a porous substrate.

11. The method according to claim 1, wherein the artificial foam containing porous portion is cut into a cube geometry prior to scanning.

12. The method according to claim 11, wherein the cube has a volume of less than 0.5 cubic inches.

13. The method according to claim 1, wherein scanning the artificial foam to obtain a digital porous model is accomplished by micro-CT.

14. The method according to claim 1, wherein the implant is further cleaned after 3D printing.

15. The method according to claim 1, wherein the implant is further grit blasted and/or coated after 3D printing.

16. The method according to claim 1, wherein the artificial foam is a reticulated foam selected from the group consisting of polyurethane foam, carbon foam, ceramic coated carbon foam, and metal coated carbon foam.

17. The method according to claim 1, wherein the artificial foam is a reticulated foam selected from the group consisting of aluminum coated carbon foam, copper coated carbon foam, nickel coated carbon foam, silicon carbide coated carbon foam, tantalum coated carbon foam, titanium nitride coated carbon foam, titanium carbide coated carbon foam and chromium coated carbon foam.

* * * * *